United States Patent [19]
Herrick et al.

[11] Patent Number: 5,282,942
[45] Date of Patent: Feb. 1, 1994

[54] METHODS AND APPARATUS FOR SEPARATING AND MOBILIZING SOLUTES IN A SOLUTE MIXTURE

[75] Inventors: Steven S. Herrick, Anaheim Hills; James C. Sternberg, Fullerton, both of Calif.

[73] Assignee: Beckman Instruments, Inc., Fullerton, Calif.

[21] Appl. No.: 16,592

[22] Filed: Jan. 22, 1993

[51] Int. Cl.$^5$ .................. G01N 27/26; G01N 27/447
[52] U.S. Cl. .................. 204/183.2; 204/180.1; 204/182.1; 204/299 R
[58] Field of Search ............ 204/183.2, 180.1, 299 R, 204/182.1

[56] References Cited

U.S. PATENT DOCUMENTS

| | | | |
|---|---|---|---|
| 4,680,201 | 7/1987 | Hjerten | 427/230 |
| 4,725,343 | 2/1988 | Hjerten et al. | 204/183.2 |
| 4,911,808 | 3/1990 | Hjerten | 204/182.9 |
| 5,069,766 | 12/1991 | Zhu et al. | 204/180.1 |
| 5,092,972 | 3/1992 | Ghowsi | 204/182.1 |
| 5,151,164 | 9/1992 | Blanchard et al. | 204/182.1 |

OTHER PUBLICATIONS

K. Ghowski and R. J. Gale "Field Effect Electrophoresis" Journal of Chromatography, 559 (1991) 95–101.

C. S. Lee, C. T. Wu, T. Lopes, and B. Patel, "Analysis of Separation Efficiency in Capillary Electrophoresis with Direct Control of Electrophoresis by Using an External Electric Field" Journal of Chromatography 559 (1991) 133–140.

C. T. Wu, T. L. Huang, and C. S. Lee "Dispersion Studies of Capillary Electroosmosic With Direct Control of Electroosmosis" Analytical Chemistry, vol. 65, No. 5 (1991) 568–571.

P. Tsai, B. Patel, and C. S. Lee "Direct Control of Electroosmosis and Retention Window in Micellar Electrokinetic Capillary Chromatography" Analytical Chemistry, vol. 65, No. 10 (1993) 1439–1442.

(List continued on next page.)

*Primary Examiner*—John Niebling
*Assistant Examiner*—John S. Starsiak, Jr.
*Attorney, Agent, or Firm*—William H. May; P. R. Harder; Wen Liu

[57] ABSTRACT

The present invention provides processes for isoelectric focusing ("IEF") and associated detection, which incorporates a dynamic means of electroosmotic flow ("EOF") control during IEF and/or after IEF to effect solute mobilization. In accordance with the present invention, the EOF control during IEF and/or solute mobilization after IEF are accomplished by applying an external electric field, relative to an internal electric field, to modify the electroosmotic flow in the capillary. This can be done by disposing a conductive member at one or more locations outside and along the buffer column in the capillary. The conductive member may be statically charged or caused to conduct a current to create the external required electric field. The applied external electric field may be adjusted, relative to the internal electric field, during IEF as necessary to reduce or completely suppress EOF to prevent flow of the buffer. Upon the completion of IEF (irrespective of the method of reducing or removing EOF during IEF), the external electric field is adjusted, relative to the internal electric field, such that the buffer carrying the focused solutes is moved electroosmotically through the capillary past a detection point. The present invention is applicable to internally coated capillary which suppresses EOF even in the absence of the external electric field.

20 Claims, 1 Drawing Sheet

OTHER PUBLICATIONS

M. A. Hayes and A. G. Ewing, "Electroosmotic Flow Control and Monitoring With an Applied Radial Voltage for Capillary Zone Electrophoresis" Analytical Chemistry, vol. 64, No. 5 (1992) 512–516.

C. T. Wu, T. Lopes, B. Patel, and C. S. Lee "Effect of Direct Control of Electroosmosis on Peptide and Protein Separations in Capillary Electrophoresis" Analytical Chemistry, vol. 64, No. 8 (1992) 886–891.

C. S. Lee, W. C. Blanchard, and C. T. Wu, "Direct Control of the Electroosmosis in Capillary Zone Electrophotoresis by Using an External Electric Field" Analytical Chemistry, vol. 62, No. 14 (1990) 1550–1552.

C. S. Lee, D. McManigill, C. T. Wu, and B. Patel, "Factors Affecting Direct Control of Electroosmosis Using an External Electric Field in Capillary Electrophoresis", Analytical Chemistry, vol. 63, No. 15 (1991) 1519–1523.

Hayes, Mark et al.: "Effects of Buffer pH on Electroosmotic Flow Control by an Applied Radial Voltage for Capillary Zone Electrophoresis"; Anal. Chem. 1993, vol. 65, pp. 27–31.

Applied Biosystems User Bulletin, No. 5, "Isoelectric Focusing on the 270A-HT", pp. 1–18.

METHODS AND APPARATUS FOR SEPARATING AND MOBILIZING SOLUTES IN A SOLUTE MIXTURE

BACKGROUND OF THE INVENTION

1. Field of the Invention

The present invention relates generally to methods and apparatus for focusing and mobilizing solutes of an aqueous solute mixture. More particularly, the present invention involves the mobilization of focused protein zones past a detector associated with a capillary isoelectric focusing apparatus without relying upon the application of pressure, vacuum, or buffer changes.

2. Description of Relevant Art

Recently capillary isoelectric focusing ("IEF") techniques have emerged as a powerful tool for rapidly separating, analyzing and quantitating small quantities of proteins. These techniques are based upon traditional isoelectric focusing principles and are carried out in free solution of amphoteric buffers within a length of capillary tubing. Capillary isoelectric focusing is a form of capillary electrophoresis which separates or fractionates proteins according to their isoelectric point ("pI"). Typically, protein focusing processes are performed in a medium containing a mixture of ampholytes which form a pH gradient extending along the length of the capillary in the presence of an electric field. The IEF process involves applying an electric field through the ampholytes along the interior of the capillary. Under the influence of the electric field, the solutes at one end of the capillary migrate along the capillary length until each solute reaches a location at which the pI of the solute corresponds to the local pH (i.e. a location of zero net charge).

After the migration is complete and all the solutes are stabilized at their respective focused zones, the solute zones are mobilized past a detector to determine the relative migration distance or time of each solute. Then, from plots of elution time versus pI of known solutes focused according to the same conditions, the pI corresponding to each unknown protein is determined.

Since IEF is a process in which the solutes seek their "focus" position in a separation medium, it is important that the medium remains stationary during migration of the solutes to their respective positions in the medium. A phenomenon which frustrates this objective is electroosmosis flow ("EOF") which inherently occurs in electrophoresis being carried out in silica containing capillary tubes. This phenomenon arises from a potential, termed the zeta potential, which develops between the inner surface of the silica tubing and a diffuse layer in the buffer adjacent the inner surface. More particularly, the silica capillary tubing surface tends to ionize to form an anion rich surface, and the diffuse layer carries cationic counter-ions to the anions on the ionized surface. In the presence of an electric field along the buffer, the charged buffer migrates to the anode or cathode. The exact direction of buffer flow and the rate of solvent flow within the capillary depend on the polarity and magnitude of this potential.

While it is desirable to maintain the medium stationary during IEF, it is also desired that the medium be mobilized after IEF for analysis of the separated solutes carried therein. Accurate and precise detection results depend upon mobilizing or moving the focused zones carried in the medium past a suitable detector while preserving the spatial relationship of the protein separation zones as focused within the capillary.

A number of different methods for mobilizing focused solutes in order to detect their stabilized locations within the buffer gradient have been suggested. For example, one method involves pumping a solution through the capillary to move the zones by hydrodynamic flow. A related method utilizes a vacuum technique to pull the zones past a suitable detector. A major problem associated with each of these methods is that hydrodynamic flow is characterized by a parabolic flow profile which causes zone broadening or distortion, thereby affecting accuracy and precision of the analytical process.

Another method for mobilizing focused proteins is disclosed in U.S. Pat. Nos. 4,911,808 and 4,725,343 and involves producing a pH shift in the separation medium within the column subsequent to focusing the mixture components. This effectively restores a charge to the ampholytic buffers and causes them to move under the influence of the internally applied voltage. Unfortunately, at zones where the pH gradient is characterized by very high or very low pI's, band broadening and non-linear effects occur during the mobilization. This in turn results in analytical error for proteins detected within these extreme zones. Additionally, many focusing procedures may be limited in pH by the instability of the separated molecules or by the alteration of charges on the molecules which alter their electrophoretic mobilities.

To this date, no effective means of EOF control as well as solute mobilization in an IEF process have been devised.

Accordingly, it is an objective of the present invention to provide an improved IEF process which incorporates means for controlling EOF during IEF.

It is another objective of the present invention to provide an effective means for mobilizing isoelectrically focused solutes for detection after IEF while avoiding hydrodynamic flow and associated band broadening.

It is further an objective of the present invention to couple EOF control and solute mobilization by using the same means.

SUMMARY OF THE INVENTION

The present invention provides processes for IEF and associated detection, which incorporates a dynamic means of EOF control during IEF and/or after IEF to effect solute mobilization. In accordance with the present invention, the EOF control during IEF and/or solute mobilization after IEF are accomplished by applying an external electric field, relative to an internal electric field, to modify the EOF in the capillary. This can be done by disposing a conductive member at one or more locations outside and along the buffer column in the capillary. The conductive member may be statically charged or caused to conduct a current to create the required external electric field. The applied external electric field may be adjusted, relative to the internal electric field, during IEF to the extent to reduce or completely suppress EOF to prevent flow of the buffer. Upon the completion of IEF (irrespective of the method of reducing or removing EOF during IEF), the external electric field is adjusted, relative to the internal electric field, such that the buffer carrying the focused solutes are moved electroosmotically through the capillary past a detection point. The present invention is applicable to internally coated capillary which suppresses EOF even in the absence of the external electric field.

DETAILED DESCRIPTION OF THE INVENTION

The present description is of the best presently contemplated mode of carrying out the invention. This description is made for the purpose of illustrating the general principles of the invention and should not be taken in a limiting sense. The scope of the invention is best determined by reference to the appended claims.

Figure 1:
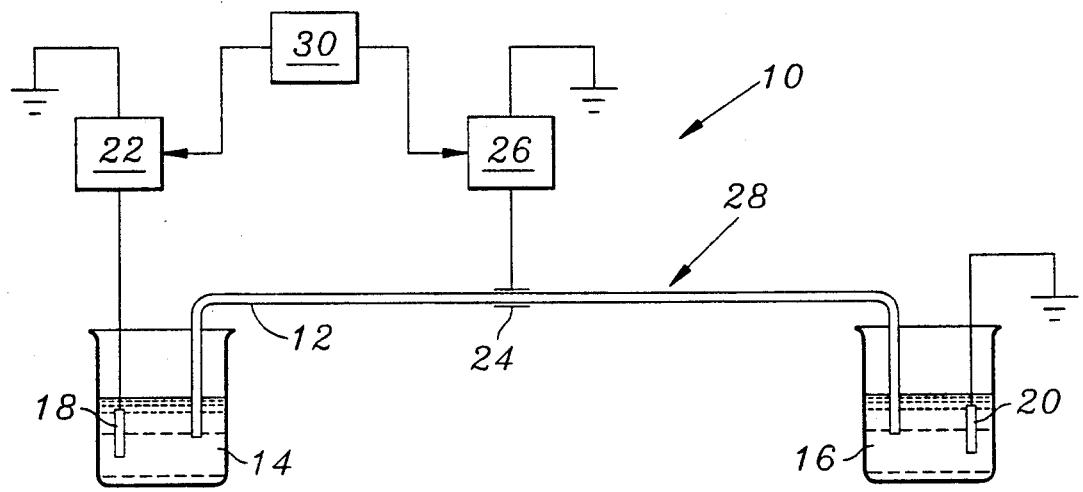
FIG. 1 is a schematic drawing of an apparatus for capillary IEF having the EOF control using an external field in accordance with one embodiment of the present invention.

Referring to FIG. 1, an apparatus 10 for conducting IEF in accordance with one embodiment of the present invention is schematically shown. The column for separation of solutes is a capillary 12 which is preferrably made of fused silica. Typically capillaries used for IEF have an inside diameter on the order of 25-500 μm. The internal surface of the capillary wall may have a coating in accordance with established prior art which reduces the effect of electroosmosis. The outside surface may also be coated for improved structural integrity. The capillary 12 supports a column of ampholyte buffer as in conventional IEF. The ends of the capillary are in communication with a buffer contained in reservoirs 14 and 16. Electrodes 18 and 20 are disposed in the buffer in the reservoirs 14 and 16. A variable power supply 22 (e.g. 0-30 KV) applies via the electrodes 18 and 20 the required voltage to create an internal electric field across the buffer along the capillary to carry out IEF. A mixture of solutes have been introduced into one end of the capillary (in the illustrated embodiment the capillary end close to the electrode 18) by any one of the established methods known in the field prior to initiating the internal electric field for IEF.

In accordance with the present invention, a conductive member 24 is disposed along the capillary 12 outside of the buffer column in the capillary. It is to be understood that the term "outside" in reference to the buffer includes the configurations where: a) the conductive member 24 is embedded in the capillary wall but not in contact with the buffer; b) in contact with the outside coated or uncoated surface of the capillary wall; or c) spaced apart from the capillary wall, with or without intermediate material between the capillary wall and the conductive member 24. It has been found that when a voltage is applied to the conductive member 24, an external electric field (as referenced to the internal electric field applied for IEF) is created across the capillary which modifies the EOF along the capillary. The voltage may be supplied by a variable power supply 26 capable of delivering, for example, 0 to +/−30 KV. It is theorized by Herrick et al. in a concurrently filed U.S. patent application Ser. No. 08/007677 entitled CAPILLARY ELECTROPHORESIS APPARATUS WITH IMPROVED ELECTROOSMOTIC FLOW CONTROL (assigned to the assignee of the present invention, and incorporated by reference herein) that the applied external field modifies the zeta potential in the diffused layer in the buffer near the inside capillary wall. By appropriately adjusting the output of the power supply 26 in relation to the voltage output of the power supply 22, it has been found that the EOF in the capillary may be substantially suppressed or caused to flow in either directions at varying speed along the capillary depending on the influence (magnitude and polarity) of the external electric field.

The conductive member 24 may be in the form of a metal ring or a band of conductive paint around the capillary 12 as schematically illustrated in FIG. 1. It has been found that the span and location of the conductive member around and along the capillary 12 may vary and the EOF control effect can still be achieved (see Herrick et al patent application, supra, and FIG. 2 and accompanying description below). For example, the conductive member may be a planar member disposed adjacent or in contact with the capillary.

The EOF control function of the conductive member 24 in the context of IEF will now be described. As was mentioned previously, under the influence of the internal electric field during IEF, the buffer is driven to flow by electroosmosis. With the EOF control capability of the conductive member 24, the buffer EOF can be reduced or even suppressed to maintain stationary by appropriately adjusting the external electric field by varying the voltage applied to the conductive member 24. The voltage to be applied to the conductive member 24 to achieve zero EOF depends on the strength of the internal electric field and the zeta potential at the buffer-capillary interface. This voltage may be determined by observing the movement of a neutral marker in the buffer while adjusting the external electric field by varying the applied power supply 26.

Upon completion of IEF, the internal electric field is maintained and the external field is removed by reducing or turning off the power supply 26. This would allow the inherent EOF to mobilize the buffer to carry the focused solute zones through the capillary past a detector 28 for analysis. If desired, the external electric field may be adjusted opposite to that for achieving zero EOF so as to increase the EOF rate. In addition, the internal electric field may be adjusted in conjunction with the external electric field to obtain the desired balance between the charges in the diffused layer and the internal electric field strength for achieving a particular EOF.

It is to be understood that EOF control during IEF may not be necessary if the inside wall of the capillary has been treated with a polymeric coating which substantially suppresses formation of zeta potential and hence EOF in the presence of an internal electric field. In this case, the EOF control by means of the external electric field is carried out after IEF for mobilization of the solute zones. It is expected that the applied external electric field in this case induces the formation of zeta potential even in the presence of such capillary coating. A suitable coating is described, for example, in U.S. Pat. No. 4,680,201 to Hjerten, which is incorporated by reference herein.

The coordination of the power supplies 22 and 26 to accomplish EOF control during and /or after IEF can be performed by a microprocessor controller 30 which is programmed to control the power supplies to deliver the appropriate amount of voltages to obtain the desired internal and external electric fields at the appropriate timing. The length of time required for completion of IEF may be determined empirically by experiment and the controller 30 programmed to switch control from EOF reduction during IEF to buffer mobilization after IEF.

Figure 2:
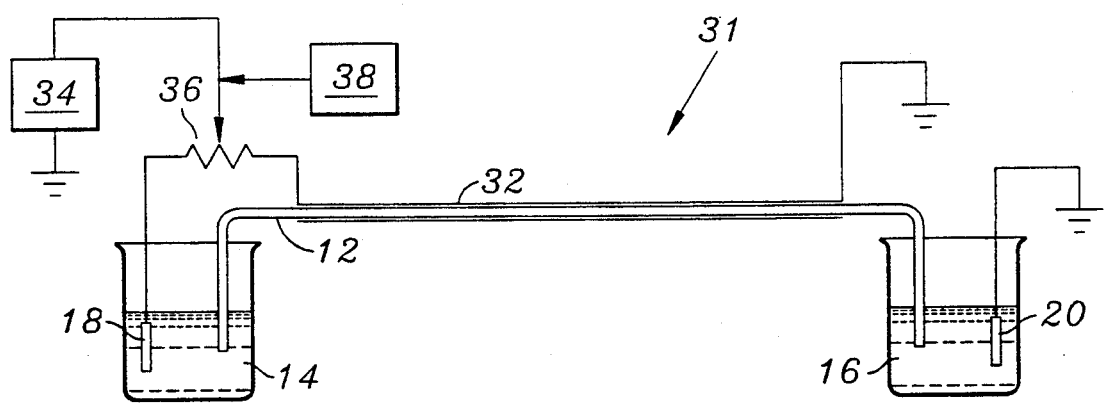
FIG. 2 is a schematic drawing of an apparatus for capillary IEF having the EOF control using an external field in accordance with another embodiment of the present invention.

It is noted in FIG. 1 that the conductive member 24 is electrically isolated (i.e. there is no complete electrical circuit and therefore no current flows in the member) and it is merely being statically charged by the applied voltage. FIG. 2 shows an alternate embodiment of an apparatus 31 for IEF in which a current is passed through a conductive member 32 disposed around a capillary 12 to accomplish EOF control in an IEF process. In this embodiment, the conductive member 32 covers the substantially entire length of the capillary 12. A single power supply 34 applies voltages to the electrode 18 and one end of the conductive member 32 via a variable voltage divider 36. The other end of the conductive member 32 is grounded, thus allowing a current to pass through the member when a voltage is applied to the member. The electrodes 18 and 20 apply an internal electric field for IEF, and the conductive member 32 creates an external electric field which modifies the zeta potential at the capillary-buffer interface. The exact mechanism of EOF control is explained in detail in U.S. Pat. No. 5,151,164 to Blanchard et al. It is sufficient to mention here that by adjusting the variable voltage divider 36, the relative magnitude of the voltages applied to the conductive member 32 and the electrode 18 can be adjusted. Accordingly, the internal and external electric fields can be adjusted to obtain EOF at varying speeds in either directions along the capillary or to reduce or suppress EOF.

An IEF process can take advantage of the EOF control in this embodiment in a similar manner as the previous embodiment. EOF can be reduced or suppressed to reduce buffer flow or maintain the buffer stationary in the capillary during IEF, and EOF is subsequently initiated after IEF to mobilize the buffer. The control of the internal and external fields can be automatically controlled by a microprocessor controller 38 which is programmed to adjust the voltage divider to establish the desired internal and external electric fields to accomplish the afore-described functions.

While the invention has been described with respect to the embodiments in accordance therewith, it will be apparent to those skilled in the art that various modifications and improvements may be made without departing from the scope and spirit of the invention. For example, capillary with an internal coating of ionizable material may be used in the IEF process described above. The degree of ionization of the ionizable coating can be controlled by the external electric field, which would influence the EOF of the buffer. Accordingly, it is to be understood that the invention is not to be limited by the specific illustrated embodiments, but only by the scope of the appended claims.

What is claimed is:

1. A process for isoelectric focusing comprising the steps of:
   providing a length of capillary having a flow path filled with a buffer suitable for isoelectric focusing;
   introducing a mixture of solutes into the buffer;
   applying an internal electric field across the buffer along the flow path of the capillary, said field causing isoelectric focusing of the solutes;
   applying an external electric field to adjust, relative to the internal field, the electroosmostic flow rate of the buffer in the capillary during application of the internal field for isoelectric focusing.

2. A process as in claim 1 further comprising the step of adjusting the external electric field to reduce the electroosmotic flow during isoelectric focusing of the solutes.

3. A process as in claim 1 further comprising the step of adjusting the external electric field to obtain a desired electroosmotic flow rate after isoelectric focusing thereby to mobilize the isoelectric focused solutes.

4. A process as in claim 1 wherein the external electric field is applied by applying a current through a conductive member disposed outside the flow path and along a section of the length of the capillary.

5. A process as in claim 1 wherein the external field is applied by applying a voltage to an electrically isolated conductive member disposed outside the flow path and at at least one location along the capillary.

6. In a capillary isoelectric focusing process in which an internal electric field is applied across a suitable buffer in a length of capillary for isoelectric focusing of sample solutes, a detection method comprising the steps of:
   after isoelectric focusing of the solutes, applying an external electric field, still in the presence of an internal electric field, so as to cause electroosmotic flow of the buffer in the capillary to thereby mobilize the solutes past a detector.

7. A process as in claim 6 wherein the external electric field is applied by applying a current through a conductive member disposed outside the flow path and along a section of the length of the capillary.

8. A process as in claim 6 wherein the external field is applied by applying a voltage to an electrically isolated conductive member disposed outside the flow path and at at least one location along the capillary.

9. A process as in claim 6 wherein the capillary has a coating on its inside wall which substantially suppresses electroosmotic flow in the absence of the external electric field during isoelectric focusing.

10. An apparatus for isoelectric focusing comprising:
    a length of capillary having a flow path filled with a buffer suitable for isoelectric focusing;
    a mixture of solutes introduced into the buffer;
    means for applying an internal electric field across the buffer along the flow path of the capillary, said field causing isoelectric focusing of the solutes;
    means for applying an external electric field to the buffer;
    means for adjusting the external electric field, relative to the internal electric field, to reduce the electroosmotic flow rate of the buffer in the capillary during application of the internal field for isoelectric focusing, and for adjusting the external electric field to obtain a desired electroosmotic flow after isoelectric focusing thereby to mobilize the isoelectric focused solutes.

11. An apparatus as in claim 10 wherein said means for adjusting the external electric field reduces the electroosmotic flow during isoelectric focusing of the solutes.

12. An apparatus as in claim 10 wherein the means for applying the external electric field includes a conductive member disposed outside the flow path and along a section of the length of the capillary, and means for applying a current through said conductive member.

13. An apparatus as in claim 10 wherein the means for applying the external field includes an electrically isolated conductive member disposed outside the flow path and at at least one location along the capillary, and means for applying a voltage to said conductive member.

14. An apparatus for isoelectric focusing comprising:
a length of capillary having a flow path filled with a buffer suitable for isoelectric focusing;
a mixture of solutes introduced into the buffer;
means for applying an internal electric field across the buffer along the flow path of the capillary, said field causing isoelectric focusing of the solutes;
means for applying an external electric field to the buffer to obtain a desired electroosmotic flow after isoelectric focusing thereby to mobilize the isoelectric focused solutes.

15. An apparatus as in claim 14 wherein the means for applying the external electric field includes a conductive member disposed outside the flow path and along a section of the length of the capillary, and means for applying a current through said conductive member.

16. An apparatus as in claim 14 wherein the means for applying the external field includes an electrically isolated conductive member disposed outside the flow path and at at least one location along the capillary, and means for applying a voltage to said conductive member.

17. An apparatus as in claim 14 wherein the capillary has a coating on its inside wall which substantially suppresses electroosmotic flow in the absence of the external electric field.

18. An apparatus as in claim 17 wherein the means for applying the external electric field includes a conductive member disposed outside the flow path and along a section of the length of the capillary, and means for applying a current through said conductive member.

19. An apparatus as in claim 17 wherein the means for applying the external field includes an electrically isolated conductive member disposed outside the flow path and at at least one location along the capillary, and means for applying a voltage to said conductive member.

20. A method of conducting isoelectric focusing of solutes, the method comprising the steps of:
providing a capillary having a coating on its inside wall which substantially suppresses electroosmotic flow in the presence of an applied internal electric field the capillary filled with a buffer suitable for isoelectric focusing and an amount of sample solutes;
applying an internal electric field across the buffer along the capillary to cause isoelectric focusing of the solutes;
applying an external electric field after said isoelectric focusing, still in the presence of an internal electric field, so as to cause electroosmostic flow of the buffer in the capillary thereby to mobilize the solutes to pass a detector at a desired speed.

* * * * *